United States Patent
Okubo et al.

(10) Patent No.: US 6,706,894 B2
(45) Date of Patent: Mar. 16, 2004

(54) THIOL COMPOUND, METHOD FOR PRODUCING THE SAME AND OPTICAL PRODUCT MADE WITH THE SAME

(75) Inventors: Tsuyoshi Okubo, Tokyo (JP); Ken Takamatsu, Tokyo (JP)

(73) Assignee: Hoya Corporation, Tokyo (JP)

( * ) Notice: Subject to any disclaimer, the term of this patent is extended or adjusted under 35 U.S.C. 154(b) by 0 days.

(21) Appl. No.: 10/301,780

(22) Filed: Nov. 22, 2002

(65) Prior Publication Data

US 2003/0114630 A1 Jun. 19, 2003

(30) Foreign Application Priority Data

Nov. 28, 2001 (JP) .......................... 2001-362377

(51) Int. Cl.$^7$ .......................... C07D 341/00; G02C 7/02
(52) U.S. Cl. .......................... 549/19; 351/159
(58) Field of Search .............................. 549/19; 351/159

(56) References Cited

U.S. PATENT DOCUMENTS

| | | | |
|---|---|---|---|
| 3,410,869 A | | 11/1968 | Bergman et al. |
| 3,492,313 A | * | 1/1970 | Bergman et al. ............. 549/19 |
| 6,458,908 B1 | * | 10/2002 | Imai et al. ................. 526/259 |
| 6,528,601 B1 | * | 3/2003 | Hara et al. ................. 526/256 |
| 6,596,841 B2 | * | 7/2003 | Tanaka et al. ............. 528/374 |

FOREIGN PATENT DOCUMENTS

| | | |
|---|---|---|
| JP | 58-164615 | 9/1983 |
| JP | 60-199016 | 10/1985 |
| JP | 02-270859 | 11/1990 |
| JP | 03-236386 | 10/1991 |
| JP | 05-148340 | 6/1993 |
| JP | 07-118390 | 5/1995 |
| JP | 09-071580 | 3/1997 |
| JP | 09-110979 | 4/1997 |
| JP | WO02/23230 A1 | 3/2002 |

OTHER PUBLICATIONS

Doyle, F.P. et al., Antituberculous Sulphur Compounds. Part II. Some Cyclic Sulphides Derived from Dimercaptoalkanoes, *Journal of Chemical Society*, pp. 2660–2665 (1960).

European Search Report dated Nov. 13, 2002.

* cited by examiner

*Primary Examiner*—Deborah C Lambkin
(74) *Attorney, Agent, or Firm*—Finnegan, Henderson, Farabow, Garrett & Dunner, LLP

(57) ABSTRACT

A thiol compound useful as a starting material for optical materials that have a high refractive index and a high Abbe's number is provided. A method for producing the same is also provided. The thiol compound may be represented by the general formula (1):

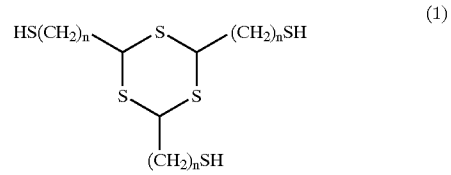

wherein n is 1 or 2. A method for producing the thiol compound represented by the general formula (1), via an intermediate, i.e., 1,3,5-trithiane having a methylene or vinyl group at the 2,4,6-positions thereof, wherein the groups at the 2-, 4-, and 6-positions may be identical or different, is also provided.

7 Claims, No Drawings

THIOL COMPOUND, METHOD FOR PRODUCING THE SAME AND OPTICAL PRODUCT MADE WITH THE SAME

CROSS-REFERENCE TO RELATED APPLICATION

The present application claims priority under 35 U.S.C. § 119 of Japanese Application No. 2001-362377, filed Nov. 28, 2001, the disclosure of which is expressly incorporated by reference herein in its entirety.

DESCRIPTION

1. Field of the Invention

The present invention relates to thiol compounds, to a method for producing the same, and to an optical product made with the same. The invention generally relates to thiol compounds that may give optical materials having a high refractive index and a high Abbe's number and having excellent heat resistance and transparency. The invention also relates to a method for producing the same and to an optical product made with the same.

2. Background of the Invention

Plastics are used for various optical applications these days, for example, for lenses and others, as being lightweight, difficult to break, and easily colored when compared with glass. Optical plastic materials include poly (diethylene glycol bisallylcarbonate) (CR-39) and poly (methyl methacrylate). These plastics, however, have a refractive index of 1.50 or less. Therefore, for example, when they are used as lens materials, the lenses produced need to be thicker for increased power, and they lose the advantage of being lightweight. In particular, powerful concave lenses are thick at their periphery, and are therefore unfavorable as causing birefringence and chromatic aberration. For spectacles, such thick lenses are often not aesthetic. To obtain thin lenses, materials with higher refractive index may be used. In general, the Abbe's number of glass and plastics decreases with the increase in their refractive index, and, as a result, their chromatic aberration increases. Accordingly, plastic materials having a high refractive index and a high Abbe's number are desired.

Plastic materials proposed as having such properties include, for example, (1) polyurethanes obtained through addition-polymerization of a polythiol having bromine in the molecule and a polyisocyanate (Japanese Patent Laid-Open No. 164615/1983); and (2) polythiourethanes obtained through addition-polymerization of a polythiol and a polyisocyanate (Japanese Patent Publication No. 58489/1992 and Japanese Patent Laid-Open 148340/1993). For the starting material, polythiol for the polythiourethanes of above (2), may be branched polythiols having an increased sulfur content (Japanese Patent Laid-Open Nos. 270859/1990 and 148340/1993), and polythiols into which is introduced a dithiane structure for increasing their sulfur content (Japanese Patent Publication No. 5323/1994 and Japanese Patent Laid-Open No. 118390/1995). Other plastic materials proposed as having such properties include (3) polymers of an alkyl sulfide having a polymerization-functional group, episulfide (Japanese Patent Laid-Open Nos. 71580/1997 and 110979/1997). However, though their refractive index is increased a little, the polyurethanes of (1) above still have a low Abbe's number and have some other drawbacks in that their lightfastness is poor, their specific gravity is high and therefore, they are not lightweight. The polythiourethanes (2), those for which the starting polythiol used has a high sulfur content, have an increased refractive index of from about 1.60 to 1.68, but their Abbe's number is lower than that of optical inorganic glass having a refractive index on the same level. Therefore, they still have a problem in that their Abbe's number must be increased more. On the other hand, one example of the alkyl sulfide polymers (3) having an Abbe's number of 36 has an increased refractive index of 1.70. The lenses obtained by using this polymer can be extremely thin and lightweight. However, plastic materials having increased Abbe's number and the refractive index are still desired.

SUMMARY OF THE INVENTION

The present invention has been made to address the problems noted above. The present invention provides thiol compounds that may give optical materials having a high refractive index and a high Abbe's number and having excellent heat resistance and transparency. The present invention also provides a method for producing the same and provides an optical product made with the same.

The present inventors have determined that thiol compounds with mercaptomethyl or mercaptoethyl groups bonded to a 1,3,5-trithiane ring are useful in solving the above-noted problems, and that the compounds may be efficiently produced in a specific method.

Specifically, the invention provides a thiol compound represented by the general formula (1):

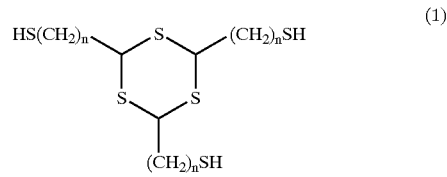

wherein n is 1 or 2.

The invention also provides a method for producing the thiol compound represented by the general formula (1) via an intermediate, i.e., 1,3,5-trithiane having a methylene or vinyl group at the 2,4,6-positions thereof, wherein the groups at the 2-, 4-, and 6-positions may be identical or different.

DESCRIPTION OF THE INVENTION

The particulars shown herein are by way of example and for purposes of illustrative discussion of the various embodiments of the present invention only. In this regard, no attempt is made to show details of the invention in more detail than is necessary for a fundamental understanding of the invention, the description making apparent to those skilled in the art how the several forms of the invention may be embodied in practice.

Unless otherwise stated, a reference to a compound or component, includes the compound or component by itself, as well as in combination with other compounds or components, such as mixtures of compounds.

The thiol compounds of the invention may be represented by the general formula (1) mentioned below, from which it is seen that the compound has three mercaptoalkyl groups bonded to the trithiane ring thereof, wherein the mercaptoalkyl groups in a given compound may be identical or different.

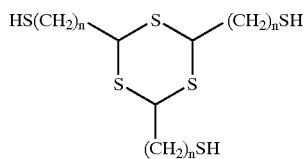

(1)

wherein n is 1 or 2.

The trithiane ring of the thiol compound represented by the general formula (1) has a high sulfur content, in which the atomic refraction is high and which therefore significantly increases the refractive index of the polymers obtained by using the thiol compounds of the invention. In addition, the polymerization-functional, terminal thiol groups in the thiol compound contribute toward introducing sulfur atoms into the main chain of the polymers of the compound, and therefore, the refractive index of the polymers obtained by using the thiol compounds of the invention is further increased. In general, the Abbe's number of amorphous materials is apt to decrease with the increase in the refractive index thereof. One problem with polymers having high sulfur content is that the electron resonance of sulfur is remarkable, therefore often significantly reducing the Abbe's number. However, the thiol compounds of the invention are free from this problem. Another cause of the increase in the refractive index is the decrease in the molar volume thereof. This is often seen in polymers having a high crosslinking density and a strong intermolecular force. The thiol compounds of the invention have three polymerization-functional groups, and the refractive index of its polymers is increased especially by the former effect. In the general formula (1), the increase in the number $\underline{n}$ lowers the sulfur content and the crosslinking density, therefore giving polymers having a reduced refractive index. Accordingly, $\underline{n}$ is generally 1 or 2. In addition, since the glass transition temperature (Tg) of the polymers obtained by using the thiol compounds of the invention lowers with the increase in $\underline{n}$ in the general formula (1), $\underline{n}$ is generally 1 or 2 in order to obtain polymers having good heat resistance.

For example, the thiol compound represented by the general formula (1) of the invention includes 2,4,6-tris(mercaptomethyl)-1,3,5-trithiane and 2,4,6-tris(mercaptoethyl)-1,3,5-trithiane.

A method for producing a thiol compound represented by the general formula (1) may comprise forming a 1,3,5-trithiane having methylene or vinyl groups at the 2,4,6-positions thereof, and reacting the 1,3,5-trithiane having methylene or vinyl groups at the 2,4,6-positions thereof to give the thiol compound represented by the general formula (1).

Another method for producing the thiol compound represented by the general formula (1) may comprise the following steps:
(a) reacting chloroacetaldehyde/3-chloropropanal with hydrogen sulfide to obtain 2,4,6-tris(chloromethyl)-1,3,5-trithiane/2,4,6-tris(chloroethyl)-1,3,5-trithiane;
(b) adding a base to remove hydrogen chloride from the compound obtained in step (a) to obtain 2,4,6-trimethylene-1,3,5-trithiane/2,4,6-triethylene-1,3,5-trithiane;
(c) adding thioacetic acid in the presence of a radical generator; and
(d) reducing the S-acetylated compound obtained in step (c) to give 2,4,6-tris(mercaptomethyl)-1,3,5-trithiane/2,4,6-tris(mercaptoethyl)-1,3,5-trithiane.

As a typical example of the method for producing the thiol compound of the invention, synthesis of 2,4,6-tris(mercaptomethyl)-1,3,5-trithiane (a compound of the general formula (1) wherein n is 1) is shown as Scheme 1 mentioned below. Concretely, an aqueous 40 wt. % chloroacetaldehyde solution is dissolved in 70 wt. % sulfuric acid, and hydrogen sulfide is introduced thereinto at −20 to 40° C. for 2 to 100 hours to give 2,4,6-tris(chloromethyl)-1,3,5-trithiane. Alternatives to sulfuric acid as the acid solvent include any of 60/40 (v/v) 95 wt. % sulfuric acid-acetic acid, hydrogen sulfide-saturated acetic acid, ether, or 95 wt. % ethanol. To the resulting methanol solution of the thus-formed chlorine compound is added potassium hydroxide with which the chlorine compound is processed at −10 to 40° C. for 0.5 to 10 hours for removal of hydrogen chloride from it to give 2,4,6-trimethylene-1,3,5-trithiane. To this compound is added thioacetic acid at 0 to 100° C. for 6 to 100 hours in the presence of a radical generator (e.g., 2,2'-azobis(isobutyronitrile), 2,2'-azobis(dimethylvaleronitrile), 4-hydroxycyclohexylphenylketone, and benzoylperoxide), and the resulting S-acetylated compound is then reduced with lithiumaluminum hydride at −10 to 50° C. for 0.5 to 6 hours to give 2,4,6-tris(mercaptomethyl)-1,3,5-trithiane (a compound of the general formula (1) wherein n is 1). 2,4,6-Tris(mercaptoethyl)-1,3,5-trithiane (a compound of the general formula (1) wherein n is 2) is obtained in the same manner as above, except that 3-chloropropanal is used in place of chloroacetaldehyde.

Scheme 1:

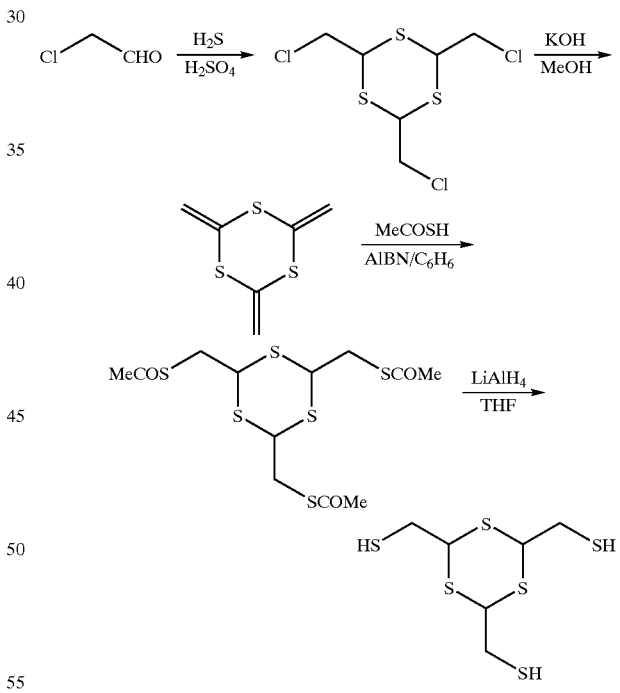

wherein Me is a methyl group.

Optical materials may be obtained by using the thiol compound of the invention. The optical materials are polymers obtained by polymerizing a polymerizable composition that contains at least one component A containing at least the thiol compound (a1) represented by the general formula (1), and at least one component B containing at least one of a compound (b1) having at least two vinyl groups in one molecule, a compound (b2) having at least two iso(thio)cyanate groups in one molecule, and a compound (b3) having at least one vinyl group and at least one iso(thio)

cyanate group in one molecule. The iso(thio)cyanate is meant to indicate both an isocyanate and an isothiocyanate.

In addition to the compound (a1) represented by the general formula (1) therein, the at least one component A may additionally contain one or two or more different types of compounds (a2) having a mercapto group and/or a hydroxyl group in one molecule, with the total number of the mercapto group and the hydroxyl group in one molecule being 2 or more, for suitably improving the physical properties of the polymer. Concretely, the compound (a2) includes trimethylolpropane, 1,2-ethanedithiol, 1,3-propanedithiol, tetrakismercaptomethylmethane, pentaerythritol tetrakismercaptopropionate, pentaerythritol tetrakismercaptoacetate, 2-mercaptoethanol, 2,3-dimercaptopropanol, 1,2-dihydroxy-3-mercaptopropane, 4-mercaptophenol, 1,2-benzenedithiol, 1,3-benzenedithiol, 1,4-benzenedithiol, 1,3,5-benzenetrithiol, 1,2-dimercaptomethylbenzene, 1,3-dimercaptomethylbenzene, 1,4-dimercaptomethylbenzene, 1,3,5-trimercaptomethylbenzene, toluene-3,4-dithiol, and 4,4'-dihydroxyphenyl sulfide. The amount of the compound (a1) represented by the general formula (1) is generally from 0.1 to 100 mole %, and often from 10 to 100 mole % relative to the total amount of the at least one component A.

Examples of the vinyl group-containing compound (b1) for the at least one component B includes divinylbenzene, ethylene glycol di(meth)acrylate, trimethylolpropane tri (meth)acrylate, as well as urethane-modified (meth) acrylates, epoxy-modified (meth)acrylates and polyester-modified (meth)acrylates each having at least two (meth) acryloxy groups in one molecule. The (meth)acrylate is meant to indicate both acrylate and methacrylate; and (meth) acryloxy group is meant to indicate both an acryloxy group and a methacryloxy group.

Examples of the iso(thio)cyanate group-containing compound (b2) for the at least one component B include xylylene diiso(thio)cyanate, 3,3'-dichlorodiphenyl-4,4'-diiso (thio)cyanate, 4,4'-diphenylmethane diiso(thio)cyanate, hexamethylene diiso(thio)cyanate, 2,2',5,5'-tetrachlorodiphenyl-4,4'-diiso(thio)cyanate, and tolylene diiso(thio)cyanate. Other examples of the compound (b2) having at least one cyclohexyl ring are bis(iso(thio) cyanatomethyl)cyclohexane, bis(4-iso(thio) cyanatocyclohexyl)methane, bis(4-iso(thio)cyanatomethyl) cyclohexyl)methane, cyclohexane diiso(thio)cyanate, isophorone diiso(thio)cyanate, 2,5-bis(iso(thio) cyanatomethyl)bicyclo[2.2.2]octane, 2,5-bis(iso(thio) cyanatomethyl)bicyclo[2.2.1]heptane, 2-iso(thio) cyanatomethyl-3-(3-iso(thio)cyanatopropyl)-5-iso(thio) cyanatomethyl-bicyclo[2.2.1]heptane, 2-iso(thio) cyanatomethyl-3-(3-iso(thio)cyanatopropyl)-6-iso(thio) cyanatomethyl-bicyclo[2.2.1]heptane, 2-iso(thio) cyanatomethyl-2-[3-iso(thio)cyanatopropyl]-5-iso(thio) cyanatomethyl-bicyclo[2.2.1]heptane, 2-iso(thio) cyanatomethyl-2-(3-iso(thio)cyanatopropyl)-6-iso(thio) cyanatomethyl-bicyclo[2.2.1]heptane, 2-iso(thio) cyanatomethyl-3-(3-iso(thio)cyanatopropyl)-6-(2-iso(thio) cyanatoethyl)-bicyclo[2.2.1]heptane, 2-iso(thio) cyanatomethyl-3-(3-iso(thio)cyanatopropyl)-6-(2-iso(thio) cyanatoethyl)-bicyclo[2.2.1]heptane, 2-iso(thio) cyanatomethyl-2-(3-iso(thio)cyanatopropyl)-5-(2-iso(thio) cyanatoethyl)-bicyclo[2.2.1]heptane, and 2-iso(thio) cyanatomethyl-2-(3-iso(thio)cyanatopropyl)-6-(2-iso(thio) cyanatoethyl)-bicyclo[2.2.1]heptane.

Examples of the compound (b3) having both vinyl and iso(thio)cyanate groups for the at least one component B include 2-(meth)acryloxyethyl iso(thio)cyanate and (meth) acryloyl iso(thio)cyanate. If the at least one component B has a vinyl group, the polymerization-functional groups in the at least one component A may all be mercapto groups. In that case, when the at least one component A has a hydroxyl group, the degree of polymerization does not increase, whereby the mechanical properties of the polymers produced may be reduced.

If desired, the optical materials may contain additives such as UV absorbent, antioxidant, discoloration inhibitor, and fluorescent dye for improving their weather resistance. Also if desired, catalysts may be used for improving the polymerization reactivity. For example, organic peroxides, azo compounds, and basic catalysts are effective for improving the reactivity between the mercapto group and the vinyl group. Organotin compounds and amine compounds are effective for improving the reactivity between the mercapto group or the hydroxyl group and the iso(thio)cyanate group.

If desired, an episulfide compound may be added to these components to fabricate the optical products. Examples of the episulfide compound include linear organic compounds such as bis(β-epithiopropylthio)methane, 1,2-bis(β-epithiopropylthio)ethane, 1,3-bis(β-epithiopropylthio) propane, 1,2-bis(β-epithiopropylthio)propane, 1-(β-epithiopropylthio)-2-(β-epithiopropylthiomethyl) propane, 1,4-bis(β-epithiopropylthio)butane, 1,3-bis(β-epithiopropylthio)butane, 1-(β-epithiopropylthio)-3-(β-epithiopropylthiomethyl)butane, 1,5-bis(β-epithiopropylthio)pentane, 1-(β-epithiopropylthio)-4-(β-epithiopropylthiomethyl)pentane, 1,6-bis(β-epithiopropylthio)hexane, 1-(β-epithiopropylthio)-5-(β-epithiopropylthiomethyl)hexane, 1-(β-epithiopropylthio)-2-[(2-β-epithiopropylthioethyl)thio]ethane, 1-(β-epithiopropylthio)-2-[(2-(2-β-epithiopropylthioethyl) thioethyl)thio]ethane and compounds derived from them by substituting at least one hydrogen of the episulfide group therein with a methyl group; branched organic compounds such as tetrakis(β-epithiopropylthiomethyl)methane, 1,1,1-tris(β-epithiopropylthiomethyl)propane, 1,5-bis(β-epithiopropylthio)-2-(β-epithiopropylthiomethyl)-3-thiapentane, 1,5-bis(β-epithiopropylthio)-2,4-bis(β-epithiopropylthiomethyl)-3-thiapentane, 1-(β-epithiopropylthio)-2,2-bis(β-epithiopropylthiomethyl)-4-thiahexane, 1,5,6-tris(β-epithiopropylthio)-4-(β-epithiopropylthiomethyl)-3-thiahexane, 1,8-bis(β-epithiopropylthio)-4-(β-epithiopropylthiomethyl)-3,6-dithiaoctane, 1,8-bis(β-epithiopropylthio)-4,5-bis(β-epithiopropylthiomethyl)-3,6-dithiaoctane, 1,8-bis(β-epithiopropylthio)-4,4-bis(β-epithiopropylthiomethyl)-3,6-dithiaoctane, 1,8-bis(β-epithiopropylthio)-2,4,5-tris(β-epithiopropylthiomethyl)-3,6-dithiaoctane, 1,8-bis(βepithiopropylthio)-2,5-bis(β-epithiopropylthiomethyl)-3,6-dithiaoctane, 1,9-bis(β-epithiopropylthio)-5-(β-epithiopropylthiomethyl)-5-[(2-β-epithiopropylthioethyl) thiomethyl]-3,7-dithianonane, 1,10-bis(β-epithiopropylthio)-5,6-bis[(2-β-epithiopropylthioethyl) thio]-3,6,9-trithiadecane, 1,11-bis(β-epithiopropylthio)-4,8-bis(β-epithiopropylthiomethyl)-3,6,9-trithiaundecane, 1,11-bis(β-epithiopropylthio)-5,7-bis(β-epithiopropylthiomethyl)-3,6,9-trithiaundecane, 1,11-bis(β-epithiopropylthio)-5,7-[(2-β-epithiopropylthioethyl) thiomethyl]-3,6,9-trithiaundecane, 1,11-bis(β-epithiopropylthio)-4,7-bis(β-epithiopropylthiomethyl)-3,6, 9-trithiaundecane, and compounds derived from them by substituting at least one hydrogen of the episulfide group therein with a methyl group; cycloaliphatic organic compounds such as 1,3- and 1,4-bis(β-epithiopropylthio) cyclohexane, 1,3- and 1,4-bis(β-epithiopropylthiomethyl)

cyclohexane, bis[4-(β-epithiopropylthio)cyclohexyl]methane, 2,2-bis[4-(β-epithiopropylthio)cyclohexyl]propane, bis[4-(β-epithiopropylthio)cyclohexyl]sulfide, 2,5-bis(β-epithiopropylthiomethyl)-1,4-dithian, 2,5-bis(β-epithiopropylthioethylthiomethyl)-1,4-dithian, and compounds derived from them by substituting at least one hydrogen of the episulfide group therein with a methyl group; aromatic organic compounds such as 1,3- and 1,4-bis(β-epithiopropylthio)benzene, 1,3- and 1,4-bis(β-epithiopropylthiomethyl)benzene, bis[4-(β-epithiopropylthio)phenyl]methane, 2,2-bis[4-(β-epithiopropylthio)phenyl]propane, bis[4-(β-epithiopropylthio)phenyl]sulfide, bis[4-(β-epithiopropylthio)phenyl]sulfone, 4,4'-bis(β-epithiopropylthio)biphenyl, and compounds derived from them by substituting at least one hydrogen of the episulfide group therein with a methyl group. These compounds may be used either singly or in combination with each other.

Using the thiol compounds of the invention, optical materials can be produced, for example, according to the method mentioned below.

A uniform composition containing the above-mentioned polymerizable composition and other optional additives is first prepared, and this is cast into a glass or metal mold combined with a resin gasket, and heated and cured therein, according to a method of casting polymerization. If desired, the mold may be subjected to mold release or a mold releasing agent such as an acid phosphate ester may be added to the composition, for facilitating good release of the molded resin from the mold. The polymerization temperature varies depending on the compounds to be used, but is generally from −20° C. to +150° C.; and the polymerization time is from about 0.5 to 72 hours. After having been thus polymerized and released from the mold, the polymer may be readily colored with an ordinary disperse dye in water or in an organic solvent. For facilitating the dyeing, a carrier may be added to the dye dispersion, or the dyeing bath may be heated. Though not limited thereto, the thus-obtained optical materials are especially favorable for optical products such as plastic lenses.

The thiol compounds of the invention have three mercaptoalkyl groups bonded to the center trithiane ring, and are favorable for starting materials for optical materials. The optical materials obtained by using the thiol compounds of the invention have a high refractive index and a high Abbe's number, and have excellent heat resistance and transparency. Therefore, they are suitable for materials for optical products, for example, for lenses such as those for spectacles and cameras, and also for prisms, optical fibers, substrates for recording media such as optical discs and magnetic discs, as well as for color filters, IR-absorbing filters, etc.

EXAMPLES

The invention is described more concretely with reference to the following Examples, which, however, are not intended to restrict the scope of the invention. The physical properties of the thiol compounds obtained in the Examples, and those of the polymers obtained in the following Application Examples and Comparative Application Examples were measured according to the methods mentioned below.
Physical Properties of Thiol Compounds The refractive index ($n_D$) and the Abbe's number ($v_D$) were measured at 25° C. with an Abbe's refractometer, DR-M4 manufactured by Atago Co., Ltd.
Physical Properties of Polymers 1) Refractive index ($n_D$) and Abbe's number ($v_D$): Measured in the same manner as above.

2) Appearance: Visually checked.

3) Heat resistance: Measured with a TMA analyzer manufactured by Rigaku International Corporation. Concretely, using a pin having a diameter of 0.5 mm, TMA of each sample was measured under a load of 98 mN (10 gf) at a heating rate of 1° C./min. From the peak temperature appearing in the chart, the heat resistance was evaluated.

4) Transparency: Using a UV spectrometer, UV-330 manufactured by Hitachi, Ltd., the 550 nm UV transmittance was measured, from which the transparency was evaluated.

Example 1

Production Example of 2,4,6-Tris(Mercaptomethyl)-1,3,5-Trithiane (T1) (the General Formula (1) Wherein n is 1)

70 wt. % (v/v) sulfuric acid (100 ml) was bubbled with hydrogen sulfide for 30 minutes at 0° C., to which was dropwise added 40 wt. % chloroacetaldehyde (17.5 ml) at 0° C. over 7.5 hours. Still at the temperature, this was further bubbled with hydrogen sulfide for 24 hours. The aqueous solution of the upper layer was removed through decantation, and the residue soluble in dichloromethane (150 ml) was washed with water (25 ml×3 times), dried over anhydrous magnesium sulfate, and filtered. The solvent was evaporated away, and a pale yellow crude product (9.5 g) was obtained. The crude product was washed with hexane (40 ml×4 times), hexane/ether (6/1) (50 ml×2 times) and hot hexane (30 ml×2 times), and dried in vacuum to obtain a white crystal, i.e., 2,4,6-tris(chloromethyl)-1,3,5-trithiane (2.50 g). To a methanol (25 ml) solution of this compound (0.3 g, 1.06 mmoles) was added a methanol solution (5 ml) of potassium hydroxide (0.62 g, 11 mmoles) all at a time with vigorous stirring at room temperature, and this was further stirred at room temperature for 75 minutes. The reaction mixture was diluted with water (30 ml), and extracted with dichloromethane (20 ml×5 times), and the resulting extract was dried over anhydrous magnesium sulfate and filtered. The solvent was evaporated away from the filtrate, and a yellow oily residue, i.e., 2,4,6-trimethylene-1,3,5-trithiane, (150 mg) was thus obtained. To a benzene (1 ml) solution of this compound (0.47 g) were added thioacetic acid (0.68 g) and azobisbutyronitrile (0.2 mg), and the mixture was stirred in an argon atmosphere at 60° C. for 2 hours. The solvent was evaporated away from the reaction mixture to obtain a crude product of an S-acetylated derivative. To a THF (10 ml) solution of the crude product (4.02 g) was added dropwise an ether solution (12 ml) of 1.0 M lithiumaluminum hydride at 0° C. Then, this was stirred at room temperature for 2 hours. The reaction mixture was acidified with 1 N hydrochloric acid, and extracted with benzene, and the resulting extract was washed with water until it became neutral, followed by drying over anhydrous magnesium sulfate. The benzene was evaporated away from the extract, and the resulting residue was recrystallized from chloroform/methanol to obtain a crystal of 2,4,6-tris(mercaptomethyl)-1,3,5-trithiane (1.73 g) (m.p.=42 to 46° C.).

For identifying its structure, the compound was analyzed and its data are shown below.

$^1$H-NMR (solvent, CDCl$_3$; internal standard substance, TMS): δ 1.7 (t, 3H), δ 2.82 (m, 6H), δ 4.37–4.63 (t,t,m, 3H).

IR (KBr tablet): 662, 740, 800, 860, 922, 1025, 1190, 1250, 1420, 2540 cm$^{-1}$.

Example 2
Production Example of 2,4,6-Tris(Mercaptoethyl)-1,3,5-Trithiane (T2) (the General Formula (1) Wherein n is 2)

A liquid product, i.e., 2,4,6-tris(mercaptoethyl)-1,3,5-trithiane, was obtained in the same manner as in Example 1, except that chloropropanal was used in place of chloroacetaldehyde. Its refractive index ($n_D$) was 1.684, and its Abbe's number ($v_D$) was 32.4.

For identifying its structure, the compound was analyzed and its data are shown below.

$^1$H-NMR (solvent, CDCl$_3$; internal standard substance, TMS): δ 1.8 (t, 3H), δ 2.54 (m, 6H), 62.78 (m, 6H), δ 4.33–4.54 (t,t,m, 3H).

IR (KBr tablet): 664, 742, 808, 865, 925, 1036, 1197, 1255, 1422, 2536 cm$^{-1}$.

Application Example 1
Production of Optical Material Made of Polymer

A mixture of T1 (0.2 moles) obtained in Example 1, m-xylylene diisocyanate (XDI) (0.3 moles) and dibutyltin dilaurate (DBTDL) (1×10$^{-5}$ moles) was uniformly stirred at 50° C., and cast into a mold of two glass sheets for lens production. In the mold, the mixture was polymerized under heat at 60° C. for 10 hours, then at 90° C. for 5 hours and then at 120° C. for 3 hours to obtain a lens-shaped polymer. The physical properties of the thus-obtained polymer are given in Table 1. As shown in Table 1, the polymer obtained in this Application Example 1 was colorless and transparent. Its refractive index ($n_D$) was extremely high, i.e., 1.71; its Abbe's number ($v_D$) was also high, i.e., 36; and its heat resistance (132° C.) and transparency (92%) were excellent. Accordingly, the polymer obtained was favorable for optical materials.

Application Examples 2 to 5
Production of Optical Material Made of Polymer

Lens-shaped polymers were produced in the same manner as in Application Example 1, except that the component A containing the thiol compound of the invention, the component B having iso(thio)cyanate and/or vinyl groups, and the polymerization catalyst as shown in Table 1 were used, and the polymerization condition was suitably varied. See also definitions of abbreviations that follow Table 1. The physical properties of the polymers are given in Table 1. As shown in Table 1, the polymers obtained in Application Examples 2 to 5 are also colorless and transparent. Their refractive index ($n_D$) was extremely high, i.e., from 1.68 to 1.76; their Abbe's number ($v_D$) was also high, i.e., from 35 to 38; and their heat resistance (99 to 124° C.) and transparency (89 to 94%) were excellent.

Comparative Application Example 1
Production of Optical Material Made of Polymer As shown in Table 1, a mixture of 0.1 moles of pentaerythritol tetrakismercaptopropionate (PETMA), 0.2 moles of m-xylylene diisocyanate (XDI), and 1.0×10$^{-4}$ moles of dibutyltin dichloride (DBTDCL) was uniformly stirred, and cast into a mold of two glass sheets for lens production. In the mold, the mixture was polymerized under heat at 50° C. for 10 hours, then at 60° C. for 5 hours and then at 120° C. for 3 hours to obtain a lens-shaped polymer. The physical properties of the thus-obtained polymer are given in Table 1. As shown in Table 1, the polymer obtained in this Comparative Application Example 1 was colorless and transparent (92%), but its $n_D/v_D$ was 1.59/36, or that is, its refractive index was low. In addition, its heat resistance (86° C.) was inferior.

Comparative Application Examples 2 and 3
Production of Optical Material Made of Polymer Lens-shaped polymers were produced in the same manner as in Comparative Application Example 1, except that the materials as shown in Table 1 were used. Their physical properties are given in Table 1. As shown in Table 1, the polymer of Comparative Application Example 2 had an $n_D/v_D$ of 1.67/28, that is, its $n_D$ and $v_D$ were both low. Though its heat resistance (94° C.) was relatively good, it was discolored, and its transparency (81%) was low. The polymer of Comparative Application Example 3 had a relatively high $v_D$ of 36, it had good weather resistance, and it was colorless and transparent (89%). However, its heat resistance (90° C.) was not good, its $n_D$ was not so high, i.e., 1.70, and it was brittle.

TABLE 1

| Application Example No. | Component A (mole) | Component B (mole) | Polymerization catalyst (mole) | $n_D/v_D$ | Appearance | Heat resistance (° C.) | Transparency (%) |
|---|---|---|---|---|---|---|---|
| 1 | T1 (0.2) | XDI (0.3) | DBTDL (1 × 10-5) | 1.71/36 | Colorless and transparent Hard | 132 | 92 |
| 2 | T1/DMMD (0.1/0.02) | DDP (0.01) | DBTDL (4 × 10$^{-4}$) | 1.74/35 | Colorless and transparent Hard | 99 | 91 |
| 3 | T2/TMP (0.1/0.02) | DVB (0.19) | ADVN (1 × 10$^{-3}$) | 1.72/35 | Colorless and transparent Hard | 121 | 89 |
| 4 | T2 (0.1) | MEI (0.17) | ADVN/ DBTDL (2 × 10$^{-3}$/ 1 × 10$^{-5}$) | 1.68/38 | Colorless and transparent Hard | 112 | 94 |
| 5 | T1/DMM (0.1/0.03) | HXDI/HMDI (0.12/0.06) | DBTDCL (1.5 × 10$^{-4}$) | 1.76/37 | Colorless and transparent Hard | 124 | 93 |

| Comparative Application Example No. | Starting formulation (mole) | Polymerization catalyst (mole) | $n_D/v_D$ | Appearance | Heat resistance (° C.) | Transparency (%) |
|---|---|---|---|---|---|---|
| 1 | PETMA/XDI | DBTDCL | 1.59/36 | Colorless and | 86 | 92 |

TABLE 1-continued

|   | | | | | | |
|---|---|---|---|---|---|---|
|   | (0.1/0.2) | (1.0 × 10⁻⁴) | | transparent Hard | | |
| 2 | TMB/XDI (0.2/0.3) | DBTDCL (1.5 × 10⁻⁴) | 1.67/28 | Pale yellow and transparent Hard | 94 | 81 |
| 3 | BES (0.1) | TEA (1.0 × 10⁻⁴) | 1.70/36 | Colorless and transparent Brittle | 90 | 89 |

Abbreviations in Table 1
T1:        2,4,6-Tris(mercaptomethyl)-1,3,5-trithiane
T2:        2,4,6-Tris(mercaptoethyl)-1,3,5-trithiane
DMMD:    2,5-Bis(mercaptomethyl)-1,4-dithiane
TMP:      1,2,3-Trimercaptopropane
DMM:     Dimercaptomethane
XDI:      m-Xylylene diisocyanate
DDP:     1,5-Diisocyanato-2,4-dithiapentane
DVB:     Divinylbenzene
MEI:      2-Methacryloxyethyl isocyanate
HXDI:     1,3-Bis(isocyanatomethyl)cyclohexane
HMDI:     Bis(4-isocyanatocyclohexyl)methane
DBTDL:   Dibutyltin dilaurate
ADVN:    Azobisdimethylvaleronitrile
DBTDCL:  Dibutyltin dichloride
PETMA:   Pentaerythritol tetrakismercaptopropionate
TMB:     1,3,5-Trimercaptobenzene
BES:      Bis(epithiomethyl)sulfide
TEA:      Triethylamine While the invention has been described in connection with certain embodiments so that aspects thereof may be more fully understood and appreciated, it is not intended to limit the invention to these particular embodiments. On the contrary, it is intended to cover all alternatives, modifications and equivalents as may be included within the scope of the invention as defined by the appended claims.

What is claimed is:

1. A method for producing a thiol compound represented by the general formula (1):

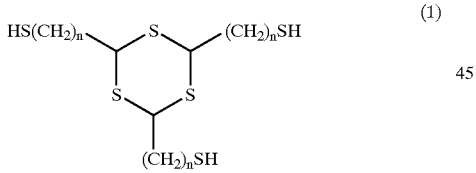

(1)

wherein n is 1 or 2, and wherein the method comprises:
  forming a 1,3,5-trithiane having methylene or vinyl groups at the 2,4,6-positions thereof; and
  reacting the 1,3,5-trithiane having methylene or vinyl groups at the 2,4,6-positions thereof to give the thiol compound represented by the general formula (1).

2. An optical product comprising a polymer obtained by using, as monomers, at least one component A comprising at least one thiol compound (a1) represented by the general formula (1):

(1)

wherein n is 1 or 2,
and at least one component B comprising at least one of:
  compound (b1) having at least two vinyl groups in one molecule,
  compound (b2) having in one molecule at least two isocyanate groups, at least two isothiocyanate groups, or at least two isocyanate groups and at least two isothiocyanate groups, and
  compound (b3) having in one molecule (1) at least one vinyl group; and (2) at least one isocyanate group, at least one isothiocyanate group, or at least one isocyanate group and at least one isothiocyanate group.

3. The optical product according to claim 2, wherein the at least one component A further comprises a compound (a2) having in one molecule at least one of a mercapto group and a hydroxyl group, with a total number of the mercapto group and the hydroxyl group in one molecule being at least 2.

4. The optical product according to claim 1, wherein the polymer is a polymer obtained by using, as a further monomer, at least one episulfide compound.

5. The optical product according to claim 2, wherein the optical product comprises a plastic lens.

6. The optical product according to claim 3, wherein the optical product comprises a plastic lens.

7. The optical product according to claim 4, wherein the optical product comprises a plastic lens.

* * * * *

UNITED STATES PATENT AND TRADEMARK OFFICE
CERTIFICATE OF CORRECTION

PATENT NO. : 6,706,894 B2
DATED : March 16, 2004
INVENTOR(S) : Tsuyoshi Okubo et al.

It is certified that error appears in the above-identified patent and that said Letters Patent is hereby corrected as shown below:

Column 12,
Line 54, "claim 1," should read -- claim 2, --.

Signed and Sealed this

Twenty-second Day of February, 2005

JON W. DUDAS
*Director of the United States Patent and Trademark Office*